(12) United States Patent
Bharadwaj et al.

(10) Patent No.: US 7,497,861 B2
(45) Date of Patent: Mar. 3, 2009

(54) CHISEL SYSTEM FOR OSTEOCHONDRAL IMPLANTS AND A SURGICAL PROCEDURE INVOLVING SAME

(75) Inventors: Jeetendra Bharadwaj, Memphis, TN (US); Jeffrey H. Nycz, Collierville, TN (US); Daniel Shimko, Germantown, TN (US)

(73) Assignee: Warsaw Orthopedic, Inc.

( * ) Notice: Subject to any disclaimer, the term of this patent is extended or adjusted under 35 U.S.C. 154(b) by 364 days.

(21) Appl. No.: 11/343,156

(22) Filed: Jan. 30, 2006

(65) Prior Publication Data

US 2007/0191873 A1 Aug. 16, 2007

(51) Int. Cl.
*A61B 18/18* (2006.01)
*A61B 17/56* (2006.01)
(52) U.S. Cl. .......................... 606/84; 606/79
(58) Field of Classification Search .......... 606/79, 606/83, 84, 85, 82, 174, 86 R
See application file for complete search history.

(56) References Cited

U.S. PATENT DOCUMENTS

| 5,059,195 | A | * | 10/1991 | Gray | 606/84 |
| 5,957,946 | A | * | 9/1999 | Shuler et al. | 606/184 |
| 5,961,522 | A | * | 10/1999 | Mehdizadeh | 606/79 |
| 6,306,142 | B1 | * | 10/2001 | Johanson et al. | 606/79 |
| 2006/0009774 | A1 | * | 1/2006 | Goble et al. | 606/85 |

OTHER PUBLICATIONS

U.S. Appl. No. 11/340,024, filed Jan. 26, 2006, Nycz, et al.
U.S. Appl. No. 11/339,194, filed Jan. 25, 2006, Nycz, et al.
U.S. Appl. No. 11/338,926, filed Jan. 25, 2006, Bharadwaj, et al.
U.S. Appl. No. 11/317.985, filed Dec. 23, 2005, Lyons.
U.S. Appl. No. 11/340,884, filed Jan. 27, 2006, Shimko, et al.
U.S. Appl. No. 11/339,694, filed Jan. 25, 2006, Gil.

* cited by examiner

*Primary Examiner*—Eduardo C Robert
*Assistant Examiner*—Ellen Rust
(74) *Attorney, Agent, or Firm*—Haynes and Boone, LLP

(57) ABSTRACT

A chisel system for harvesting an implantable graft from an area of a human having a cartilage overlying a condyle, according to which a module is provided that has one end connected to a handle. A cutting surface is formed at the other end of the module that cuts through the cartilage and condyle.

12 Claims, 2 Drawing Sheets

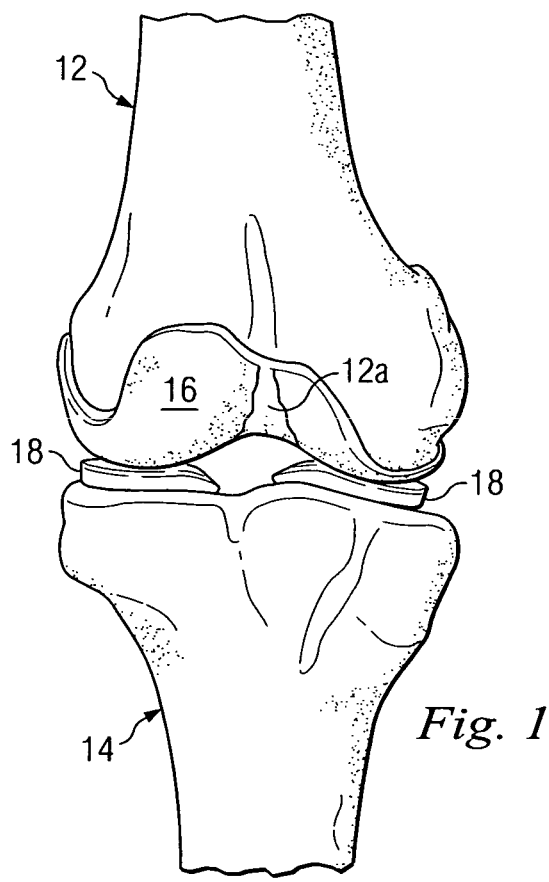
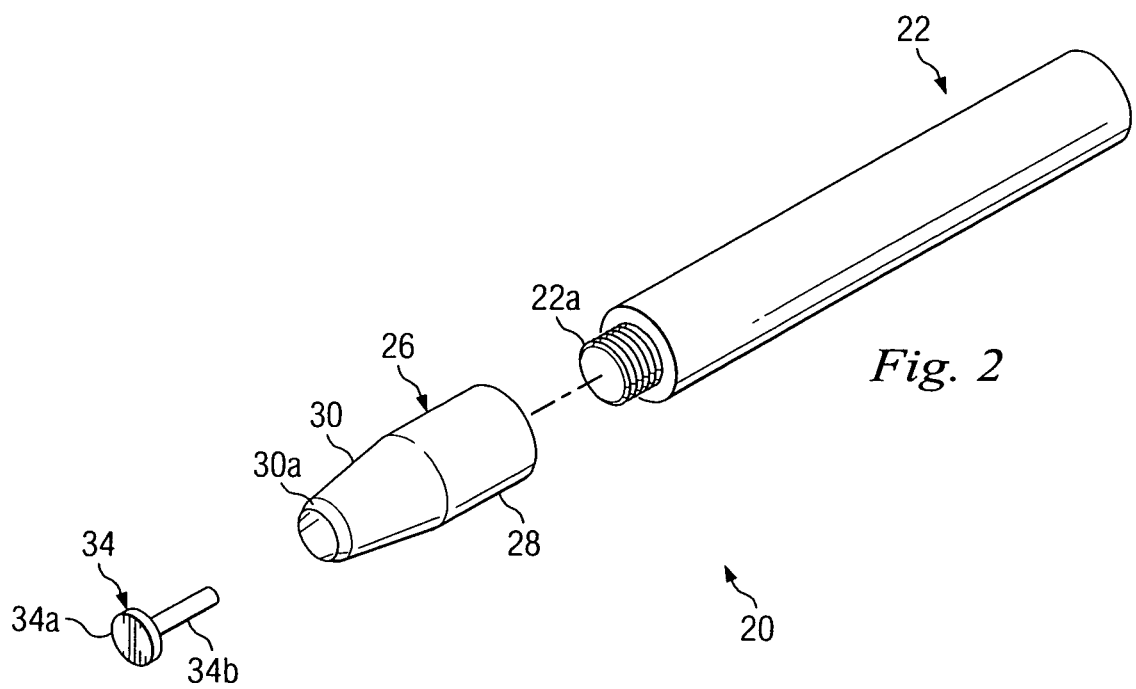

CHISEL SYSTEM FOR OSTEOCHONDRAL IMPLANTS AND A SURGICAL PROCEDURE INVOLVING SAME

BACKGROUND

This invention relates to a chisel system and, more particularly, to an improved modular chisel system for cutting an opening to receive an implant in an osteochondral implant procedure.

In the human body, the knee consists of three articulating components—a femur, a tibia, and a patella—that are held in place by various ligaments. The corresponding chondral areas of the femur and the tibia form a hinge joint, and the patella protects the joint. Portions of the latter areas, as well as the underside of the patella, are covered with an articular cartilage, which allow the femur and the tibia to smoothly glide against each other without causing damage.

The articular cartilage often tears, usually due to traumatic injury (often seen in athletics) and degenerative processes (seen in older patients). This tearing does not heal well due to the lack of nerves, blood vessels and lymphatic systems; and the resultant knee pain, swelling, and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" or "OATS" has been used to repair articular cartilages. This procedure involves removing injured tissue from the articular defect and drilling cylindrical openings in the base of the defect and underlying bone. Cylindrical plugs or grafts, consisting of healthy cartilage overlying bone, are usually obtained by using a chisel to punch them out from another area of the patient, typically from a lower load-bearing region of the joint under repair, or from a donor patient. The harvested grafts are then implanted in the openings.

in these cases, the chisels used to harvest the grafts are, for the most part, one-piece designs that consist essentially of a blade portion extending from a handle portion. Thus, once the grafts are harvested, they remain in the hollow, distal end portion of the chisel and must be removed from that end. This often causes damage to the graft, and in most cases to the cartilage portion of the graft.

Also, the cutting end of the chisels are blunt and thus can cause damage, in the form of high mechanical deformation, as the cartilage portion of the graft is punched out during the harvesting procedure. Further, each chisel can cut only one size graft, which requires a series of chisels for cutting a series of grafts having different dimensions. However, to provide a separate chisel for each size graft is expensive.

Therefore what is need is a chisel system that overcomes the above problems.

BRIEF DESCRIPTION OF THE DRAWING

FIG. 1 is an elevational view of a human knee with certain parts removed in the interest of clarity.

FIG. 2 is an isometric, exploded view of a modular chisel system according to an embodiment of the invention.

DETAILED DESCRIPTION

Figure 3:
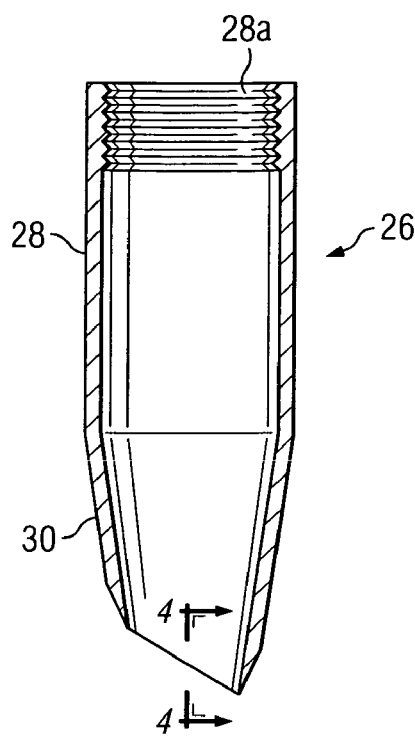
FIG. 3 is an enlarged cross-sectional view of the cutting module of the system of FIG. 2.

Referring to FIG. 1 of the drawing, the reference numeral 10 refers, in general, to a knee area of a human including a femur 12 and a tibia 14 whose respective chondral areas are in close proximity. A cartilage 16 extends over a portion of the chondral area of the femur 12, and a meniscus 18 extends between the cartilage and the tibia. The patella, as well as the tendons, ligaments, and quadriceps that also form part of the knee are not shown in the interest of clarity.

It will be assumed that a portion of the cartilage 16 extending over a chondral area 12a of the femur 14 has been damaged and removed by the surgeon, or has worn away, and it is desired to harvest a graft from another area of the patient/recipient, such as an undamaged non-load bearing area of the femur or tibia, or from a corresponding area of a donor. It will also be assumed that an opening is formed in the defect 12a for receiving the graft.

Referring to FIG. 2, a chisel system for harvesting the graft is referred to, in general, by the reference numeral 20 and includes a cylindrical handle 22 having an externally-threaded, reduced-diameter nipple 22a extending from one end thereof.

As shown in FIGS. 2 and 3, a cutting module 26 is provided that consists of a hollow cylindrical member 28, the inner surface of one end portion of which is internally threaded as shown by the reference numeral 28a, and is sized to receive the nipple 22a in threaded engagement. A hollow, frusto-conical member 30 extends from the other end of the member 28 and is formed integrally with the latter member.

A tap member 34 (FIG. 2) is also provided and consists of an enlarged head 34a disposed at one end of a solid rod, or shank, 34b. The diameter of the shank 34b is slightly less than the inner diameter of the distal end of the member 30, for reasons to be described. The tap member 34 is not connected to the module 26, but rather is used to remove a harvested graft from the module in a manner to be described.

Figure 4:
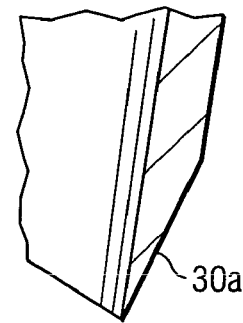
FIG. 4 is a cross-sectional view taken along the line 4-4 of FIG. 3.

As shown in FIGS. 3 and 4, the distal end portion of the member 30 is cut at an angle to form an end 30a that extends at an angle to the axis of the member. Also, the cross section of the angled end portion is tapered radially inwardly to form a relatively sharp cutting surface, or edge, 30b, for reasons to be described.

To initiate the harvesting procedure, the handle 22 (FIG. 2) is grasped and the chisel system 20 is brought down to a non-damaged area of the patient/recipient, or of a donor, such as an undamaged non-load bearing area of the femur or tibia, having a cartilage overlying a condyle. The chisel system 20 is placed perpendicularly to the latter area and forced down into the cartilage. The sharpness of the cutting edge 30a is such that it slices through the layer of cartilage. The manual force is continued and could be increased as necessary so that the cutting edge also cuts through the condyle until the desired depth is attained. During this time, the severed cartilage and condyle next to the cartilage enter the hollow distal end portion of the member 30 and move axially in the latter member. When the desired depth of cut is attained, the handle 22 is manipulated as necessary to completely sever the corresponding end of the condyle thus forming a plug, or graft (not shown) extending in the interior of the module 26.

The module 26 is then removed from the handle 22 by unscrewing the module, and the distal end of the shank 34*b* of the tap 34 is then pushed into the distal end of the member 30 where it engages the end of the condyle portion of the graft. Further pushing advances the graft though the member 30 and then though the member 28 in a direction towards the threaded end portion of the latter member. The graft is then removed from the module 30 and is ready to be treated for implantation in an opening to be formed in the defect 12*a* (FIG. 1).

It is understood that, during the above harvesting procedure, any of the meniscus 18 (FIG. 1) or related tendons, ligaments and quadriceps are removed or pushed aside as necessary to permit access to the above area to permit the harvesting of the graft.

Other modules can be provided that are identical to the module 26, but have a member similar to member 30, but with a cutting edge of a cross-section that is different than the diameter of the cutting edge 30*a*. Thus, the chisel system 20 can be provided as a kit, having one handle 22 and several modules 26, each having a different diameter cutting surface, depending on the size of the graft to be harvested.

Figure 5:
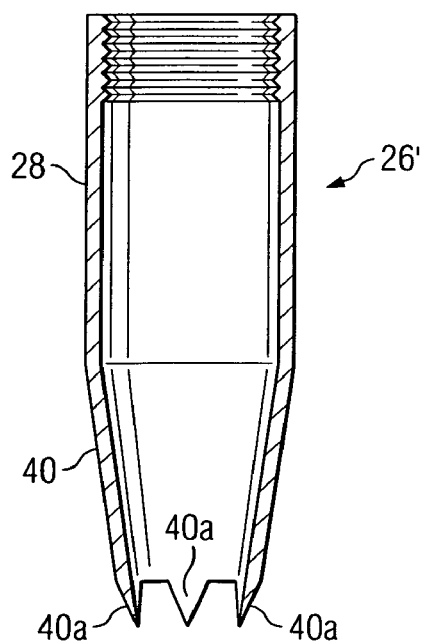
FIGS. 5 and 6 are views, similar to that of FIG. 3, but depicting alternate embodiments of the cutting module of FIG. 3.

An alternate embodiment of the module 26 is referred to in FIG. 5 by the reference numeral 26', and includes a member 28 that is identical to the member 28 of the embodiment of FIGS. 2-4. According to the embodiment of FIG. 5, a hollow, frusto-conical member 40 is provided that extends from the other end of the member 28 and is formed integrally with the latter member. A series of angularly-spaced cutting teeth 40*a* are formed at the distal end of the member 40 to form a saw tooth design. Each tooth 40*a* is tapered inwardly towards its end to define relatively sharp points and cutting edges for cutting the graft.

The harvesting procedure is initiated by bringing the module 26' into engagement with the cartilage portion of the graft to be harvested, and applying manual force so that the teeth 44*a* cut into the layer of cartilage portion and then through the condyle portion of the graft. The harvesting is then completed in accordance with the procedure discussed above and the tap 34 (FIG. 2) can be used to remove the harvested graft from the member 40, also in the same manner as described above.

Figure 6:
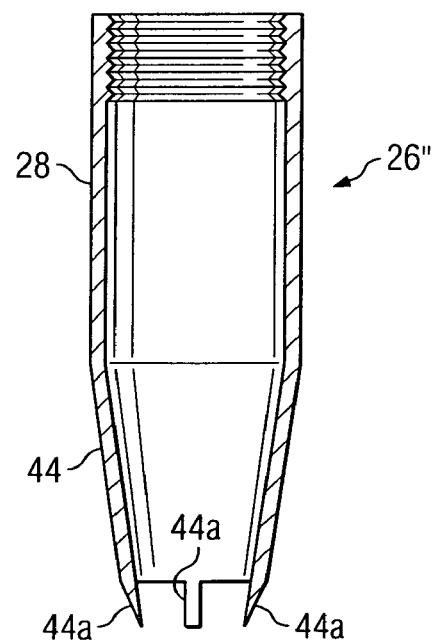

Another alternate embodiment of the module 26 is referred to in FIG. 6 by the reference numeral 26", and includes a member 28 that is identical to the member 28 of the embodiment of FIGS. 2-4. According to the embodiment of FIG. 5, a hollow, frusto-conical member 44 is provided that extends from the other end of the member 28 and is formed integrally with the latter member. Three angularly-spaced prongs 44*a* are formed at the distal end of the member 40 and are dimensioned to form sharp points and cutting edges.

The harvesting procedure is initiated by bringing the module 26" into engagement with the cartilage portion of the graft to be harvested and applying manual force so that the prongs 44*a* cut into the cartilage portion. Then, the handle 22 (FIG. 2) is rotated, causing the edges of the prongs to cut through any remaining portion of the cartilage and through the condyle portion of the graft to be harvested. The harvesting is then completed in accordance with the procedure discussed above, and the tap 34 (FIG. 2) can be used to remove the harvested graft from the member 40, also in the same manner as described above.

It can be appreciated that the above-mentioned kit can also include the modules 26' and 26", as well as variations thereof, so that the cutting surfaces can be varied in accordance with the particular application.

VARIATIONS

1. The size and shape of the cutting surfaces at the end of the members 30, 40 and 44 can vary. For example, the surfaces can have elliptical shape, a rectangular shape, or the like.

2. The configurations of the cutting surfaces at the end of the members 30, 40 and 44 can vary.

3. The number of teeth 40*a* and prongs 44*a* of the embodiments of FIGS. 5 and 6, respectively, can vary, as well as their size and/or shape.

4. The spatial references mentioned above, such as "upper", "lower", "under", "over", "between", "outer", "inner" and "surrounding" are for the purpose of illustration only and do not limit the specific orientation or location of the components described above.

5. The present invention is not limited to use with knees of humans but rather is applicable other damaged areas of all animals.

6. The graft discussed above can be harvested or prepared from another area of the patient/recipient, from another human, or from any number of anatomic sites, animal or otherwise.

7. The method and device disclosed above can be used in any surgical or experimental situation (animal species or otherwise) to harvest grafts in any anatomic region containing cartilage or bone.

Those skilled in the art will readily appreciate that many other variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A chisel system for harvesting an implantable graft, the system comprising:
    an elongated shaft extending along a longitudinal axis between a proximal portion and a distal portion, at least part of the proximal portion defining a handle and at least part of the distal portion being threaded;
    a cutting module removably engaged with the elongated shaft, the cutting module comprising:
        a proximal portion threadingly engaged with the distal portion of the elongated shaft;
        a central portion of the cutting module being generally cylindrical and extending substantially along the longitudinal axis of the elongated shaft, the central portion having an outer surface with an outer diameter and an inner surface defining an inner bore with a first inner diameter; and
        a distal portion having an inner surface and an outer surface, the inner surface tapering inwardly with respect to the inner bore of the central portion to a second inner diameter less than the first inner diameter, the outer surface tapering inwardly with respect to the outer surface of the central portion to define a plurality of cutting projections at an intersection with the inner surface; and a tap for removing an implantable graft from the cutting module through the proximal portion of the cutting module, the tap comprising a head portion and a shank portion extending from the head portion, the shank portion having a diameter less than the second inner diameter of the cutting module such that the shank portion can be inserted into the distal portion of the cutting module to urge the implantable graft out through the proximal portion of the cutting module.

2. The chisel system of claim 1, wherein the plurality of cutting projections comprise a plurality of cutting teeth annularly spaced about the distal portion of the cutting module.

3. The chisel system of claim 2, wherein each of the plurality of teeth comprises a relatively sharp point and at least one cutting edge extending proximally from the point.

4. The chisel system of claim 3, wherein each of the plurality of teeth tapers inwardly relative to the longitudinal axis.

5. The chisel system of claim 4, wherein the elongated shaft comprises a solid, monolithic component without any bores extending along its length.

6. The chisel system of claim 5, wherein the distal portion of the elongated shaft proximally bounds the inner bore of the cutting module.

7. The chisel system of claim 1, wherein the plurality of cutting projections comprise a plurality of cutting prongs annularly spaced about the distal portion of the cutting module.

8. The chisel system of claim 7, wherein each of the plurality of cutting prongs tapers inwardly relative to the longitudinal axis.

9. A chisel system for harvesting an implantable graft from anatomy having cartilage overlying a condyle such that the graft includes a cartilage portion and bone portion, the system comprising:

an elongated shaft extending along a longitudinal axis between a proximal portion and a distal portion, at least part of the distal portion being threaded;

a cutting module removably engaged with the elongated shaft and having a proximal portion, a central portion, and a distal portion;

the proximal portion of the cutting module threadingly engaged with the distal portion of the elongated shaft;

the central portion of the cutting module being generally cylindrical and extending substantially along the longitudinal axis of the elongated shaft, the central portion having an outer surface with an outer diameter and an inner surface defining an inner bore with a first inner diameter;

the distal portion having an inner surface and an outer surface, the inner surface tapering inwardly with respect to the inner bore of the central portion at a first angle relative to the longitudinal axis, a first section of the outer surface tapering inwardly with respect to the outer surface of the central portion at the first angle such that the inner surface of the distal portion and the first section of the outer surface of the distal portion extend substantially parallel to one another, and a second section of the outer surface of the distal portion tapering inwardly from the first section of the outer surface to define a cutting edge at an intersection with the inner surface, the cutting edge defining a second inner diameter less than the first inner diameter; and a tap for removing an implantable graft from the cutting module through the proximal portion of the cutting module, the tap comprising a head portion and a shank portion extending from the head portion, the shank portion having a diameter less than the second inner diameter of the cutting module such that the shank portion can be inserted through the distal portion of the cutting module to urge the implantable graft out through the proximal portion of the cutting module without contacting the cartilage portion of the implantable graft.

10. The system of claim 9, further comprising a second cutting module removably engagable with the elongated shaft and having a proximal portion, a central portion, and a distal portion;

the distal portion having an inner surface and an outer surface, the inner surface tapering inwardly with respect to an inner bore of the central portion, a first section of the outer surface tapering inwardly with respect to an outer surface of the central portion such that the inner surface of the distal portion and the first section of the outer surface of the distal portion extend substantially parallel to one another, and a second section of the outer surface of the distal portion tapering inwardly from the first section of the outer surface to define a cutting edge at an intersection with the inner surface, the cutting edge defining a third inner diameter less than the second inner diameter.

11. The system of claim 10, wherein the diameter of the shank portion of the tap is less than the third inner diameter of the second cutting module such that the shank portion can be inserted through the distal portion of the second cutting module to urge an implantable graft out through the proximal portion of the second cutting module.

12. The system of claim 10, further comprising a third cutting module removably engagable with the elongated shaft and having a proximal portion, a central portion, and a distal portion;

the distal portion having an inner surface and an outer surface, the inner surface tapering inwardly with respect to an inner bore of the central portion, a first section of the outer surface tapering inwardly with respect to an outer surface of the central portion such that the inner surface of the distal portion and the first section of the outer surface of the distal portion extend substantially parallel to one another, and a second section of the outer surface of the distal portion tapering inwardly from the first section of the outer surface to define a cutting edge at an intersection with the inner surface, the cutting edge defining a fourth inner diameter greater than the second inner diameter.

* * * * *